United States Patent [19]

Liu et al.

[11] Patent Number: 4,948,866

[45] Date of Patent: Aug. 14, 1990

[54] PROCESS FOR PREPARING 2,3-BIS(HYDROXYMETHYL) BICYCLO [2,2,1] HEPTANE AND POLYESTER THEREWITH

[75] Inventors: Kou-Chang Liu, Wayne; Suzanne B. Nelsen, Mountain Lakes, both of N.J.

[73] Assignee: GAF Chemicals Corporation, Wayne, N.J.

[21] Appl. No.: 402,577

[22] Filed: Sep. 5, 1989

[51] Int. Cl.$^5$ .............................................. C08G 63/02
[52] U.S. Cl. .................................... 528/272; 528/274; 528/280; 528/298; 528/302; 528/307; 528/308; 528/308.6; 525/168
[58] Field of Search ............... 528/272, 274, 280, 298, 528/302, 307, 308, 308.6; 525/168

[56] References Cited

U.S. PATENT DOCUMENTS

| 3,492,330 | 1/1970 | Trecker et al. | 560/354 |
| 4,248,997 | 2/1981 | Ihida | 528/272 |
| 4,400,486 | 8/1983 | Iwata et al. | 525/57 |

FOREIGN PATENT DOCUMENTS 857937 3/1973 France.

OTHER PUBLICATIONS

Birch et all, J. of Org. Chem. 21, 970–974 (1956).

Primary Examiner—John Kight, III
Assistant Examiner—S. A. Acquah
Attorney, Agent, or Firm—Walter Katz; Marilyn J. Maue; Joshua J. Ward

[57] ABSTRACT

A one-pot, two-step process for the preparation of 2,3-bis(hydroxymethyl) bicyclo [2,2,1] heptane in a non-toxic solvent is described. The compound is used for the preparation of a polyester.

1 Claim, No Drawings

PROCESS FOR PREPARING 2,3-BIS(HYDROXYMETHYL) BICYCLO [2,2,1] HEPTANE AND POLYESTER THEREWITH

BACKGROUND OF THE INVENTION

1. Field of the Invention

This invention relates to chain extenders for polyester elastomers, and, more particularly, to a one-pot, two-step process for preparing 2,3-bis(hydroxymethyl) bicyclo [2,2,1] heptane (BHMBCH) in a non-toxic solvent for the preparation of polyester therewith.

2. Description of the Prior Art

BHMBCH has been described in the literature. See Birch et al., J. of Org. Chem. 21, 970–974 (1956). The Birch synthesis involved three separate steps, namely, (1) a Diels-Alder condensation of cyclopentadiene and maleic anhydride to form an unsaturated anhydride; (2) reduction of the anhydride with lithium aluminum hydride to produce an unsaturated diol; and (3) hydrogenation over a palladium catalyst to provide the saturated diol. However, in the process, a considerable quantity of undesirable by-products were obtained during step (2), and, accordingly, four crystallizations of the crude unsaturated diol were required before the hydrogenation step (3) could be carried out effectively.

French Patent No. 857,937 described the preparation and isolation of the unsaturated diol intermediate only. The process comprised reaction between cyclopentadiene and 1,4-butenediol in dioxane solvent. However, dioxane is extremely toxic and difficult to remove completely from the reaction product.

U.S. Pat. No. 3,492,330 disclosed reactions of bridged-ring olefins, including the unsaturated diol with functional alkanes. The patentee said the unsaturated diol could be prepared from cyclopentadiene and 1,4-butenediol by a classical Diels-Alder reaction.

In summary, the prior art does not provide a commercial process for the preparation of the desired saturated diols, particularly in a one-pot, two-step process, and a non-toxic solvent which can be used for both the condensation and hydrogenation steps.

Accordingly, it is an object of the present invention to provide a new and improved process for preparing 2,3-bis(hydroxymethyl) bicyclo [2,2,1] heptane by a one-pot, two-step synthesis in a non-toxic solvent.

Another object of the invention is to provide polyester with 2,3-bis(hydroxymethyl) bicyclo [2,2,1] heptane.

These and other objects and features of the invention will be made apparent from the following more detailed description of the invention.

SUMMARY OF THE INVENTION

What is provided herein is a one-pot, two-step process for preparing 2,3-bis(hydroxymethyl) bicyclo [2,2,1] heptane (BHMBCH) in a non-toxic solvent. The process of the invention comprises reaction of cyclopentadiene and 1,4-butenediol in ethanol solvent, followed directly by hydrogenation over a suitable catalyst. The yield of the desired saturated diol is 75% or more.

In accordance with another feature of the invention, a polyester which is chain extended with BHMBCH is provided herein.

DETAILED DESCRIPTION OF THE INVENTION

The one-pot, two-step synthesis of 2,3-bis(hydroxymethyl) bicyclo [2,2,1] heptane in a non-toxic solvent according to the present invention proceeds as follows:

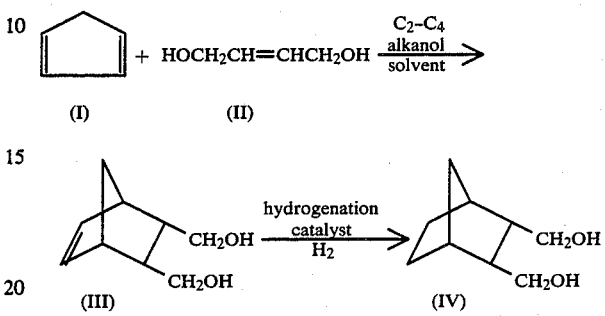

Accordingly, cyclopentadiene (I) and 2-butene-1,4-diol (II), in a molar ratio of about 1:1 to 2:1, respectively, are heated at a temperature of about 140° to 200° C. for 5 to 20 hours, in a $C_2$–$C_4$ straight or branched chain alcohol solvent, e.g. ethanol, at a solvent level of about 20 to 200% by weight of the reaction mixture, to produce the unsaturated diol intermediate (III) in high yield.

In the same pot and alcohol solvent, (III) is hydrogenated at a temperature of about 50° to 200° C. for about 1 to 20 hours with a hydrogenation catalyst to produce the saturated diol (III). Generally, the catalyst comprises about 0.05 to 5% by weight of (III). Suitable hydrogenation catalysts include palladium, platinum, rhodium, and the like, which may be supported or unsupported. Suitable supports include charcoal, calcium carbonate, etc. The overall yield of (IV) is at least 75%.

The polymerization reaction of (IV) with terephthalic acid or isophthalic acid provides chain extended polyester which are effective engineering plastics, particularly at elevated use temperatures.

The terms "terephthalic acid" and "isophthalic acid" as used herein are intended to include the condensation polymerization equivalent of such acids, i.e. their esters or ester-forming derivatives such as acid chlorides and anhydrides, or other derivatives which behave substantially like such acids in a polymerization reaction with a glycol. Dimethyl terephthalate and dimethyl isophthalate are for instance suitable starting materials for the polymers of the invention.

The invention will now be described by reference to the following working examples of the invention.

EXAMPLE 1

Preparation of 2,3-Bis(Hydroxymethyl) Bicyclo [2,2,1] Heptane (BHMBCH)

Cyclopentadiene (150 g., 2.28 moles), 2-butene-1,4-diol (150 g., 1.7 moles) and ethanol (300 g.) were charged into a 1-liter stainless steel autoclave. The autoclave was purged three times with nitrogen at 100 psig and then heated to 175° C. for 10 hours. After being cooled to room temperature, 3 g. of 5% Pd on charcoal was added to the mixture. The mixture was purged two times with nitrogen, heated to 170° C. and hydrogenated at 100 psig. The hydrogenation was completed in 7 hours.

The crude product was filtered to remove the catalyst and rotoevaporated to remove ethanol. The semisolid material obtained was distilled at 0.3-0.5 mm of Hg. The desired product comprised a forecut of 32.7 g. of material and a center cut of 150.1 g. of a pale yellow solid (m.p. 52°-56° C). The solid was recrystallized from 100 ml toluene-50 ml hexane to give 124 g. of white solid; m.p. 57°-60° C., which was identified by NMR as the title compound.

EXAMPLE 2

Preparation of Polyester from Dimethyl Terephthalate and BHMBCH

A mixture of dimethyl terephthalate (194.2 g.), BHMBCH (234.2 g.) and tetraisopropyl titanate (0.23 g.) is heated in a 1-liter resin kettle at 165° C. at 15 mm Hg. The methanol generated is continuously removed from the system. After 2 hours, the vacuum is further reduced to 1 mm Hg and the temperature is increased to 240° C. to remove excess BHMBCH. Nitrogen is introduced into the system during this period. The polymeric reaction product then is discharged.

While the invention has been described with particular reference to certain embodiments thereof, it will be understood that changes and modifications may be made which are within the skill of the art.

Accordingly, it is intended to be limited by the appended claims only, in which What is claimed is:

1. A one-pot, two-step process for the preparation of 2,3-bis(hydroxymethyl) bicyclo heptane which comprises condensing cyclopentadiene and 2-butene-1,4-diol in ethanol as solvent, and hydrogenating the unsaturated diol intermediate thus formed over a hydrogenation catalyst in the same alcohol solvent wherein the yield of the desired compound is at least 75%, wherein the condensation step is carried out at a molar ratio of cyclopentadiene to 2-butene-1,4-diol of about 1:1 to 2:1, at a temperature of about 140° to 200° C., for about 5 to 20 hours, and at a solvent level of about 20 to 200% by weight of the reaction mixture, wherein the hydrogenation step is carried out at a temperature of about 50° to 200° C. for about 1 to 20 hours, and wherein the hydrogenation catalyst is present at a condensation of about 0.05 to 5% by weight of the unsaturated diol intermediate.

* * * * *